US010105395B2

(12) United States Patent
Bruno et al.

(10) Patent No.: US 10,105,395 B2
(45) Date of Patent: *Oct. 23, 2018

(54) MICROVESICLES (MVS) DERIVED FROM ADULT STEM CELLS FOR USE IN THE THERAPEUTIC TREATMENT OF A TUMOR DISEASE

(71) Applicant: Fresenius Medical Care Deutschland GmbH, Bad Homburg (DE)

(72) Inventors: Stefania Bruno, Pinerolo (IT); Maria Beatriz Herrera Sanchez, Turin (IT); Valentina Fonsato, Pecetto Torinese (IT); Giovanni Camussi, Turin (IT); Ciro Tetta, Mirandola (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/620,164

(22) Filed: Jun. 12, 2017

(65) Prior Publication Data

US 2017/0348356 A1    Dec. 7, 2017

Related U.S. Application Data

(63) Continuation of application No. 13/581,537, filed as application No. PCT/EP2011/052945 on Feb. 28, 2011, now Pat. No. 9,717,760.

(30) Foreign Application Priority Data

Mar. 2, 2010  (EP) .................................... 10425052

(51) Int. Cl.
A61K 35/407    (2015.01)
A61K 31/00     (2006.01)
C12N 5/00      (2006.01)
C12N 5/02      (2006.01)
A61K 35/28     (2015.01)

(52) U.S. Cl.
CPC .................................. A61K 35/28 (2013.01)

(58) Field of Classification Search
None
See application file for complete search history.

(56) References Cited

U.S. PATENT DOCUMENTS 6,258,378 B1    7/2001  Schneider et al.
6,576,220 B2    6/2003  Unger
8,148,335 B2    4/2012  Moe et al.
2002/0177551 A1  11/2002  Terman
2003/0087960 A1   5/2003  Burstein
2008/0233090 A1   9/2008  Ray
2011/0014251 A1*  1/2011  Ray ...................... A61K 35/28
                                                  424/401

FOREIGN PATENT DOCUMENTS

EP      2186883            11/2006
WO   WO-2005121369 A2 * 12/2005  ......... A61K 47/6901
WO   WO 2006/126219       11/2006
WO   WO-2009036236 A1 *  3/2009  ........... C12N 15/111
WO   WO 2009/050742        4/2009
WO   WO 2009/057165        5/2009
WO   WO 2009/087361        7/2009
WO   WO 2009/105044        8/2009

OTHER PUBLICATIONS

XP-002590906, Feb. 23, 2010, Aoki et al.
Wolfers et al. Tumor-derived exosomes are a source of shared tumor rejection antigens for CTL cross-priming. Nature Medicine, vol. 7, No. 3, 2001, pp. 297-303.
Amariglio et al. Donor-derived brain tmor following neural cell . . . ; PloS Med. Feb. 17, 2009; vol. 6, issued 2, pp. 0221-0231.
Deregibus et al. Endothelial progenitor cell-derived microvesicles activate . . . ; Blood; Oct. 1, 2007; vol. 110, No. 7; pp. 2440-2448.
Bruno et al. Mesenchymal stem cell-derived microvesicles accelerate hepatic . . . ; J. Am Soc Nephrol 20; May 2009; pp. 1053-1067.
Herrera et al. Human liver stem cell-derived microvesicles accelerate hepatic . . . ; J Cell Mol Med; vol. 14, No. 6B; Jul. 24, 2009; pp. 1605-1618.
Pittenger et al. Mesenchymal stem cells and their potential as cardiac therapeutics; Circ. Res 2004; 95; pp. 9-20.
Bussaloti et al. Altered angiogenesis and survival in human tumor-derived endothelial cells; FASEB J 2003; 17.
Bussaloti et al. Vascular endothelial growth factor receptor-1 modulates vascular . . . ; Am J. Pathol Sep. 2001; vol. 159; No. 3; pp. 993-1008.
Hou et al. Experimental therapy of hepatoma with artemisinin and its derivatives: In vitro and in vivo activty . . . ; Clin Cancer Research; 2008; 14; pp. 5519-5530.

\* cited by examiner

Primary Examiner — Christopher R Tate
Assistant Examiner — Douglas F White
(74) Attorney, Agent, or Firm — Jacobson Holman, PLLC.

(57) ABSTRACT

The invention is in the field of therapeutic treatment of tumors. The inventors have found that microvesicles derived from adult stem cells exert a remarkable anti-tumor effect when administered to a patient affected by a tumor disease. Preferred microvesicles are derived from a bone marrow-mesenchymal stem cell, a glomerular mesenchymal stem cell or a non-oval liver stem cell.

10 Claims, 13 Drawing Sheets

HEPG2 TUMORS:

MICROVESICLES (MVS) DERIVED FROM ADULT STEM CELLS FOR USE IN THE THERAPEUTIC TREATMENT OF A TUMOR DISEASE

The present invention relates to the therapeutic treatment of a tumour disease.

Hematopoietic stem cells transplantation is known to exert tumor inhibitory effects in patients with solid tumor, as well as anti-tumor effects in metastatic breast, kidney, ovarian, prostate and pancreatic cancer.

Human bone marrow mesenchymal stem cells (BM-MSCs) were demonstrate to contribute to the repair of a wide variety of organs and tissues repair and experimental studies suggested that transplantation of MSCs may have a beneficial effect on functional and structural recovery in several organs including hearth, liver and kidney.

The stem cells microenvironment seems to play an essential role in preventing carcinogenesis by providing signals to inhibit proliferation and to promote differentiation.

However, the use of stem cells in therapeutic indications is less advisable given that a potential tumorigenic risk of such stem cell therapy has been reported (Amariglio N et al. Donor-derived brain tumor following neural stem cell transplantation in an ataxia telangiectasia patient. PLoS Med. 2009 Feb. 17; 6(2))

Cell-derived microvesicles (MVs) are small vesicles released by cells that express the characteristic antigens of the cell from which they originate and carry membrane and cytoplasmic constituents and have been described as a new mechanism of cell communication. Recently, the present inventors demonstrated that microvesicles derived from human endothelial progenitor cells (EPCs), BM-MSCs and hepatic liver stem cells may serve as a vehicle for transfer of genetic material (mRNA) that can reprogram target differentiated cells, as endothelial cells, tubular epithelial cells and hepatocytes (Deregibus M C et al. Endothelial progenitor cell derived microvesicles activate an angiogenic program in endothelial cells by a horizontal transfer of mRNA. Blood. 2007 Oct. 1; 110(7):2440-8; Bruno S et al. Mesenchymal stem cell-derived microvesicles protect against acute tubular injury. J Am Soc Nephrol. 2009 May; 20(5): 1053-67; Herrera M B et al. Human liver stem cell-derived microvesicles accelerate hepatic regeneration in hepatectomized rats. J Cell Mol Med. 2009 Jul. 24) and contribute to tissue regeneration and repair.

International patent application WO2009/087361 discloses producing differentiated cells by applying an inducer to a first population of undifferentiated cells and then isolating microvescicles from the differentiated cells. See in that respect the first full paragraph on page 30 of WO2009/087361. The first population of undifferentiated cells is e.g. Bone marrow mesenchymal stem cells. However, WO2009/087361 does not disclose obtaining microvesicles directly from the undifferentiated cells.

The present inventors have now found that microvesicles (MVs) derived from adult stem cells, preferably from bone marrow or glomerular mesenchymal stem cells or from non-oval liver stem cells, show remarkable anti-tumour activities both in vitro and in vivo, thereby representing an advantageous alternative over the corresponding whole stem cells for the therapeutic treatment of cancer. The anti-tumour activity of microvesicles derived from adult stem cells according to the present invention was demonstrated in vitro by measuring the effect of the microvesicles on the proliferation and apoptosis of a variety of human cancer cell lines as well as their effect on the formation of capillary-like structures. The anti-tumour activity of the microvesicles was also confirmed in an in vivo mice model by measuring the effect of MVs-treatment on tumour growth.

Figure 1A:
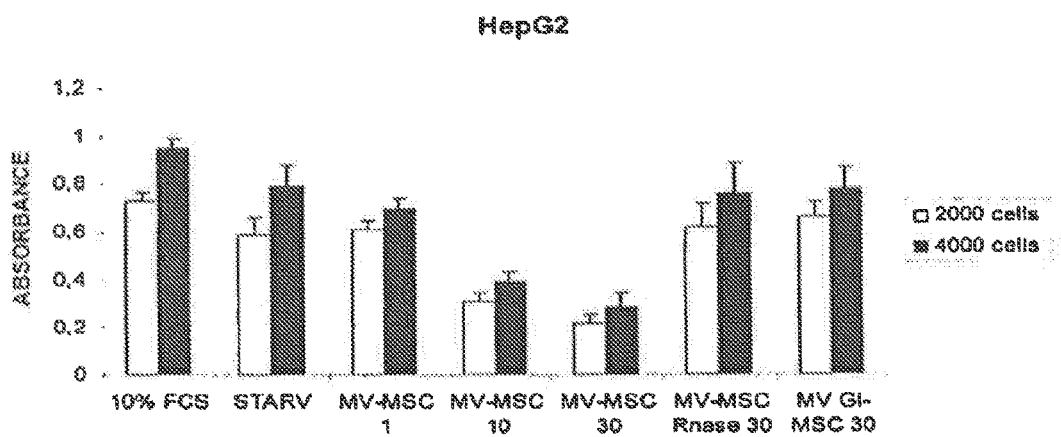
FIGS. 1 A and B graphically show the incubation results of HepG2 cells (FIG. 1A) and KS cells (FIG. 1B) with different doses of microvesicles (MVs).

The observed anti-tumour activities of microvesicles derived from adult stem cells are quite unexpected over the prior art. Preparations of mesenchymal stem cells (MSCs) are in fact known to exert a regenerative effect on some tissues. For example, bone marrow-derived MSCs are known to naturally support hematopoiesis by secreting a number of trophic molecules, including soluble extracellular matrix glycoproteins, cytokines and growth factors. Moreover, microvesicles derived from endothelial stem cells were shown in WO2009/050742 to promote angiogenesis and resistance to apoptosis, both in vitro and in vivo. In WO2009/057165 microvesicles derived from stem cells were shown to induce endothelial and epithelial regeneration of damaged tissues or organs.

In WO2009/105044 microvesicles derived from a mesenchymal stem cell are speculatively said to be suitable for use in the treatment of a high number and a great variety of diseases No experimental evidence, no theoretical explanation and no specific method for treatment of cancer is provided.

Thus, a first aspect of the present invention is a microvescicle derived from an adult stem cell for use in the therapeutic treatment of a tumour disease.

In this connection, it should be understood that the microvesicles is not necessarily derived from adult stem cells taken from the same patient to which they shall be administered. Rather, they may be derived from a different subject, prepared and maintained in the form of a medicament and then administered to a patient in need thereof. This is the so-called allogenic approach.

In a preferred embodiment, the adult stem cell is a human mesenchymal stem cell or a human liver stem cell. A preferred human liver stem cell is the human non-oval liver stem cell (HLSC) expressing both mesenchymal and embryonic stem cell markers disclosed in WO 2006/126219. This cell line is in particular characterised in that it is a non-oval human liver pluripotent progenitor cell line isolated from adult tissue which expresses hepatic cell markers and which is capable of differentiating into mature liver cells, insulin producing cells, osteogenic cells and epithelial cells and preferably express markers selected from the group comprising albumin, α-fetoprotein, CK18, CD44, CD29, CD73, CD146, CD105, CD90 and preferably do not express markers selected from the group comprising CD133, CD117, CK19, CD34, cytochrome P450.

In another preferred embodiment, the human mesenchymal stem cell is derived from human adult bone marrow (BM-MSC). In another preferred embodiment, the human mesenchymal stem cell is derived from human adult decapsulated glomeruli (Gl-MSC), as disclosed in European patent application no. 08425708.8. These cells are furthermore characterised in that they are CD133 negative, CD146 positive and CD34 negative and that they are capable of differentiating into podocytes, endothelial cells and mesangial cells and they also preferably express markers selected from the group comprising CD24, Pax-2, CD31, CD29, CD44, CD73, CD90, CD105, CD166, nanog, musashi, vimentin, nestin and preferably do not express markers selected from the group comprising α-SMA, Oct-4, CD45, cytokeratin. CD80, CD86, CD40.

According to one embodiment of the invention, the tumour disease is selected from the group consisting of liver tumour (e.g. hepatoma), epithelial tumour (e.g. Kaposi's sarcoma), breast tumour (e.g. breast adenocarcinoma), lung tumour, prostate tumour, gastric tumour, colon tumour and ovarian tumour.

Another aspect of the present invention is the use of a microvescicle derived from an adult stem cell as defined above, for preparing a medicament for the therapeutic treatment of a tumour disease as defined above.

In one embodiment, the therapeutic treatment comprises the administration of one or more cytotoxic or cytostatic agents. Suitable cytotoxic and cytostatic agents include for example Paclitaxel, Lenalidomide, Pomalidomide, Epirubicin, 5FU, Sunitinib, La-patinib, Canertinib, cyclophosphamide, doxorubicin, Lenalidomiden/Dexamethason, Po-malidomide/Dexamethasone, Carboplatin, Rapamycin, mitoxantron, oxaliplatin, docetaxel, vinorelbin, vincristine and any combination thereof. The administration of a combination of doxorubicin and/or vincristine with MVs derived from an adult stem cell is highly preferred, since such a combination has been shown to exert a synergistic effect (see FIG. 13).

The microvescicle is administered to a patient in need thereof either locally or systemically. A pharmaceutical dosage form suitable for both local and systemic administration is e.g. an injectable dosage form. By way of example, the microvescicle is administered by local intra-tumour (i.t.) injection in a solid tumour, or by i.v. injection or infusion, both in the case of a solid tumour and in the case of metastasis. A suitable MV dose to be administered depends on a plurality of factors, but it is generally comprised between 0.1 to 200 micrograms/kg body weight of the recipient, preferably 1-150 micrograms/kg body weight of the recipient, even more preferably 3-120 micrograms/kg body weight of the recipient.

The expression "microvescicle (MV) derived from an adult stem cell" as use herein refers to a membrane particle which is at least in part derived from an adult stem cell. In turn, the term "adult stem cell" includes any undifferentiated or partially undifferentiated cell which is capable of proliferating (self-renewal) and differentiating (plasticity), thereby replacing the mature cells of a specialized cell lineages which have reached the end of their life cycle. The term "adult stem cell" as used in the present description includes both stem cells having unlimited self-renewal ability and pluripotent plasticity, and progenitor cells with multipotent plasticity and, in some instances, a limited self-renewal ability. In a preferred embodiment the "adult stem cells" have pluripotent or multipotent plasticity meaning that they are capable of differentiating into at least two, more preferably at least three, distinct types of specialised, fully differentiated, mature cells.

Within the context of the present description, the expression "adult stem cell" is intended to mean a stem cell that is isolated from an adult tissue, in contrast with an "embryonic stem cell" which is isolated from the inner cell mass of a blastocyst. Adult stem cells are also known as "somatic stem cells".

Within the context of the present description, the expression "microvesicles (MV) derived from an adult stem cell is intended to mean that the microvesicles are directly derived from undifferentiated stem cells.

Within the context of the present description, the expression "directly" means that the microvesicles are derived from the undifferentiated adult stem cells without any differentiation step being carried out or having taken place before obtaining of the microvesicles.

The microvesicles derived from adult stem cells used in the present invention are generally spheroid in shape and have a diameter within the range of 100 nm to 5 μm, more typically of between 0.2 and 1 μm. If the particle is not spheroid in shape, the above mentioned values are referred to the largest dimension of the particle.

The stem cells from which the microvesicles used in the invention are obtained may be isolated as described in the experimental section of the description. The microvesicles (MVs) may then be obtained from the supernatants of the isolated stem cells, e.g. by ultracentrifugation as disclosed in the experimental section of the description. The isolated MVs may then be stored until use by freezing at very low temperature, e.g. at −80° C., in a suspension with one or more cryoprotecting agent. Suitable cryoprotecting agents are e.g. dimethylsulphoxide (DMSO) and glycerol. The use of DMSO at a concentration of 1% of the volume of the cell suspension guarantees good preservation of the cells and a limited toxic effect on re-infused patients. Other substances which may be mentioned as cryoprotecting agents are extracellular cryoprotecting agents, that is to say high molecular weight substances acting at the cell surface forming a tight barrier which reduced intracellular dehydration.

Figure 1B:
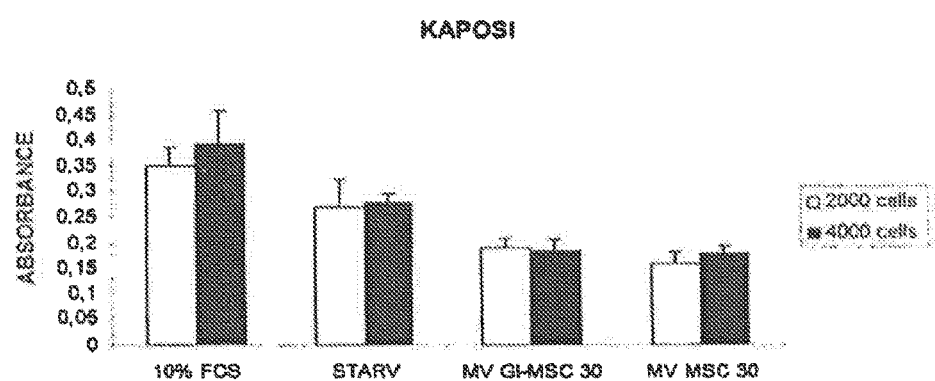

Further objects and advantages of the invention will appear more clearly from the following examples, which are provided by way of illustration only. In the example, reference is made to the following figures:

FIGS. 1 A and B show that incubation of HepG2 cells (FIG. 1A) and KS cells (FIG. 1B) with different doses of microvesicles (MVs) significantly inhibits proliferation compared to control cells incubated with vehicle alone. Proliferation of HepG2 and KS cells was evaluated by BrdU incorporation assay after 48 hours of incubation with different doses of MVs (1, 10 and 30 µg/ml) from BM-MSCs or from Gl-MSCs pre-treated or not with RNase. The results are expressed as the mean±SD of 3 experiments.

FIGS. 2 A and B show that incubation of HepG2 and KS cells with MVs significantly promotes apoptosis compared to control incubated with vehicle alone and in the same way of doxorubicin stimulation. Apoptosis of HepG2 and KS cells was evaluated by Tunel assay as the percentage of apoptotic cells after 24-hours and/or 48 hours of incubation with different doses of MVs from BM-MSC (pre-treated or not with RNase) or Gl-MSC. The results are expressed as the mean±SD of 3 experiments.

Figure 3A:
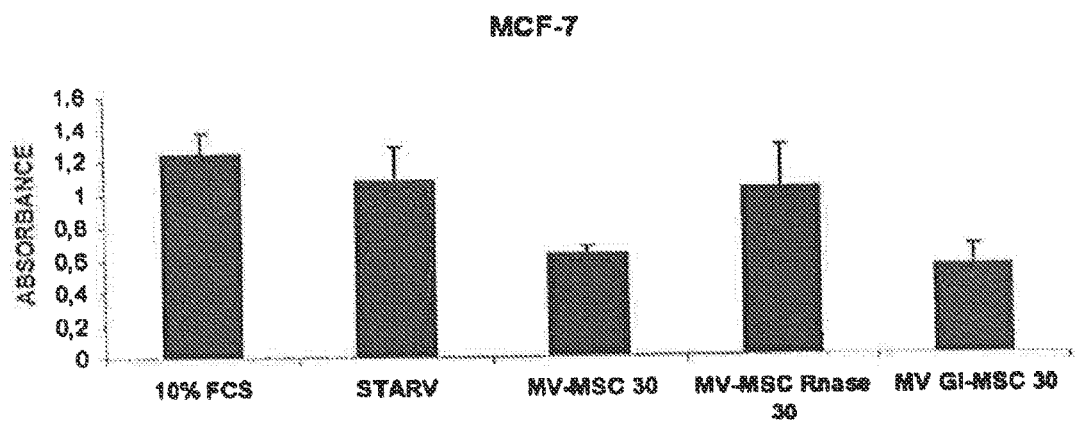
FIGS. 3A and 3B graphically show the incubation results of MCF-7 cells (FIG. 3A) and SKOV-3 cells (FIG. 3B) with 30 μg/ml of MVs from BM-MSCs for 48 hours.
Figure 3B:
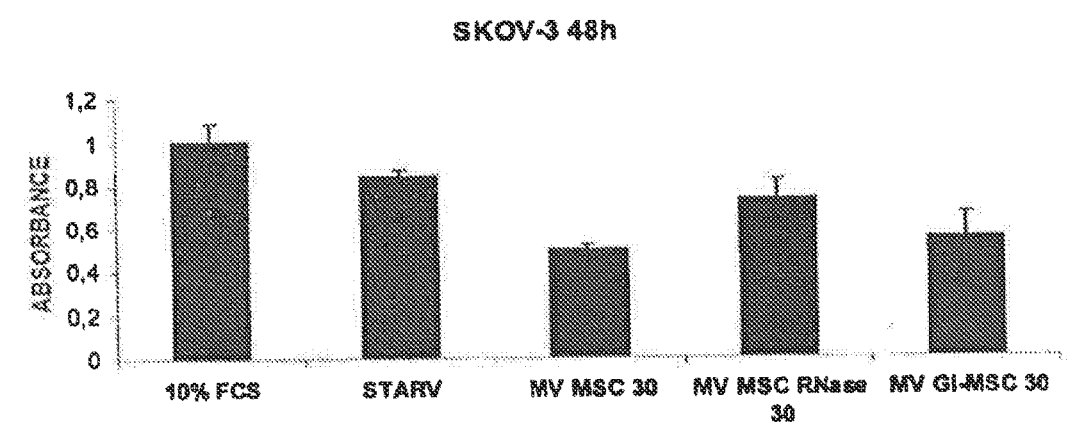

FIGS. 3A and 3B show that incubation of MCF-7 cells (FIG. 3A) and SKOV-3 cells (FIG. 3B) with 30 µg/ml of MVs from BM-MSCs for 48 hours significantly inhibits proliferation compared to control cells incubated with vehicle alone. Proliferation of MCF-7 and SKOV-3 cells was evaluated by BrdU incorporation assay after 48 hours of incubation with 30 µg/ml of MVs from BM-MSCs or from Gl-MSCs. The results are expressed as the mean±SD of 3 experiments.

Figure 4A:
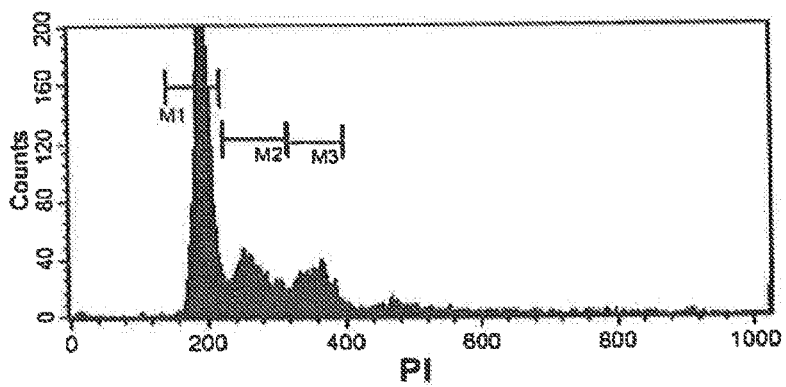
FIGS. 4A-4C graphically show the MVs from BM-MSCs inducing an increase of cells in the G0/G1 phase, especially in SKOV-3 cells.
Figure 4B:
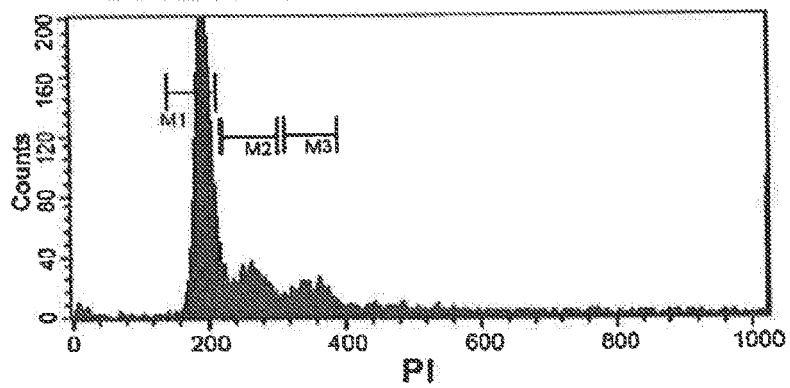
Figure 4C:
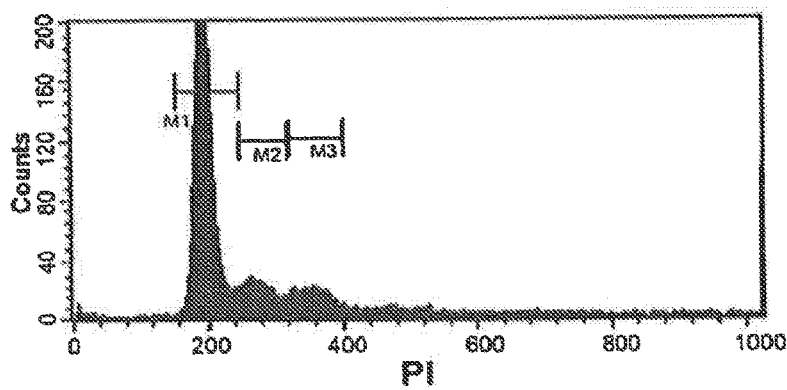

FIG. 4 shows that MVs from BM-MSCs induce an increase of cells in the G0/G1 phase, especially in SKOV-3 cells. The DNA content was measured in SKOV-3 cells cultured with 10% FCS, deprived of FCS (starvation) and in the presence of 30 µg/ml of MVs for 24 hours. An increase of the number of cells in the G0/G1 phase in the presence of MVs is observed.

Figure 5A:
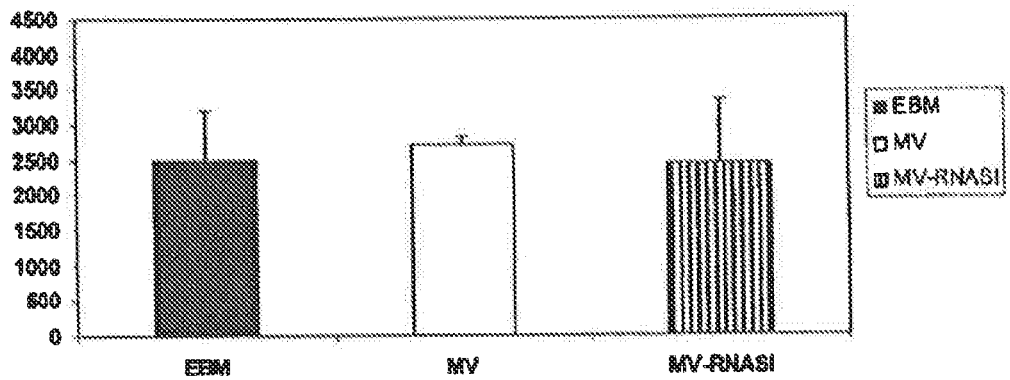
FIGS. 5A and 5B graphically show the results of experiments carried out to evaluate the effect of MVs on in vitro angiogenesis.
Figure 5B:
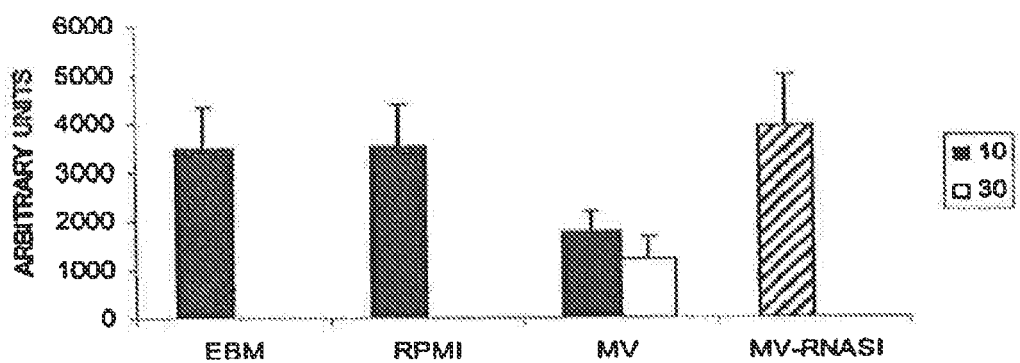

FIGS. 5A and 5B show the results of experiments carried out to evaluate the effect of MVs on in vitro angiogenesis. The ability of HUVECs and TECs to form capillary-like structures within Matrigel was evaluated.

Figure 6:
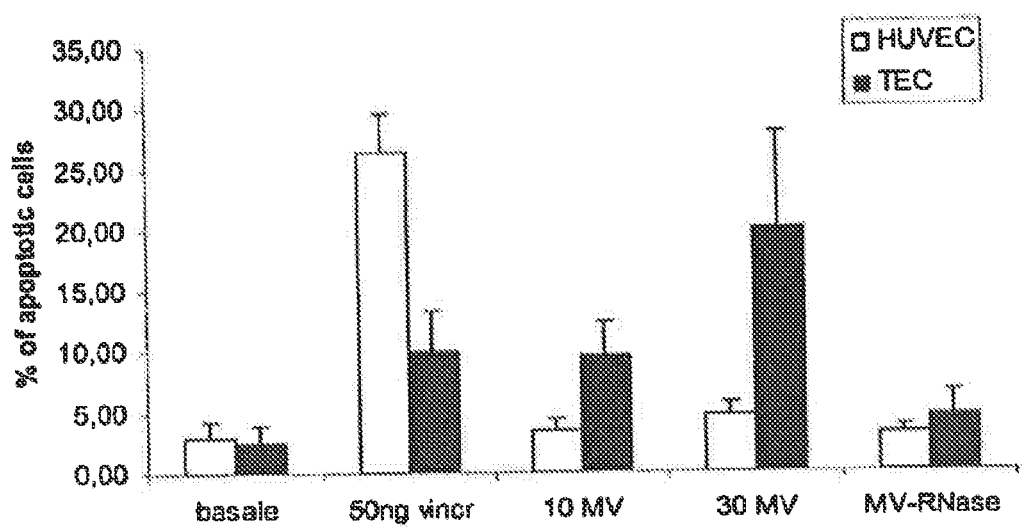
FIG. 6 graphically shows the results of experiments carried out to evaluate the effect of MVs on in vitro apoptosis.

FIG. 6 shows the results of experiments carried out to evaluate the effect of MVs on in vitro apoptosis. Apoptosis of HUVECs and TECs was evaluated by Tunel assay as a percentage of apoptotic cells after 48 hours of incubation with different doses of MVs.

Figure 7:
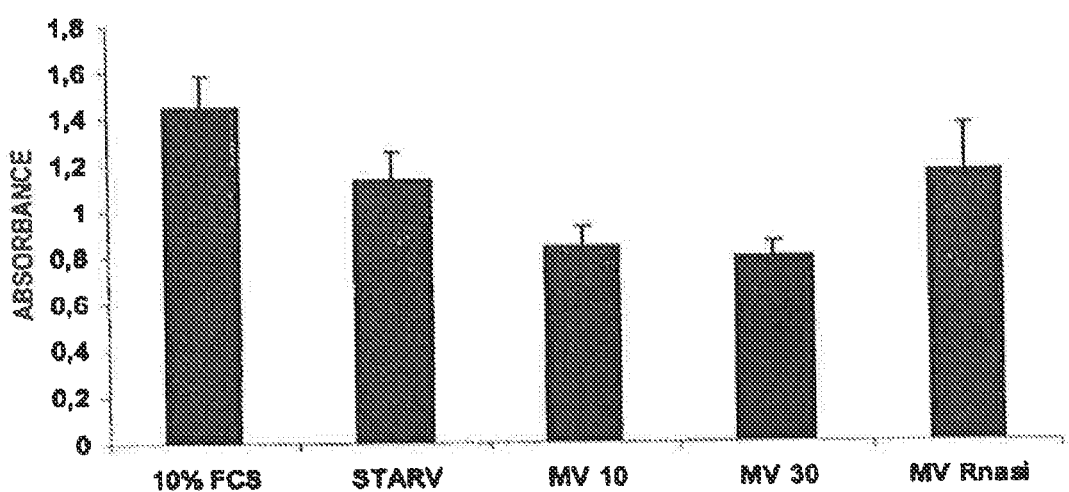
FIG. 7 graphically shows the results of experiments carried out to evaluate the effect of MVs on the proliferation of TECs.

FIG. 7 shows the results of experiments carried out to evaluate the effect of MVs on the proliferation of TECs. The proliferation of TECs was evaluated by BrdU incorporation assay after 48 hours of incubation with different doses of MV (10 and 30 µg/ml) from BM-MSC pre-treated or not with RNase. The results are expressed as the mean±SD of 2 experiments.

Figure 8:
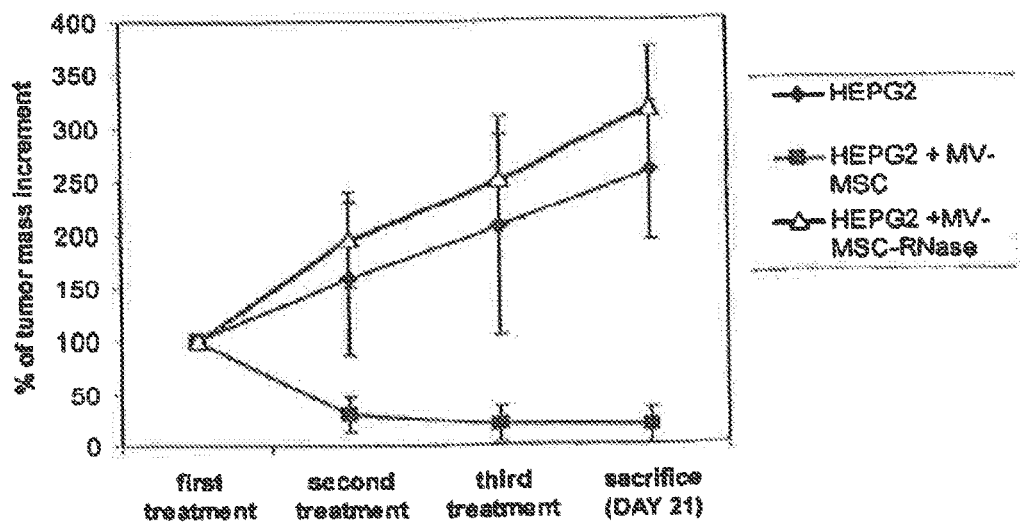
FIG. 8 graphically shows the in vivo anti-tumor activity of MVs, treated or not with RNase, intra-tumor administrated to SCID mice bearing HepG2 xenograft tumours.

FIG. 8 shows the in vivo anti-tumor activity of MVs, treated or not with RNase, intra-tumor administrated to SCID mice bearing HepG2 xenograft tumours. Tumor mass was determined by caliper measurement of two perpendicular diameters of the implant every week. The results are shown as the percentage of increment of tumour mass: the tumour mass at the first treatment (1 week after HepG2 injection) is fixed by convention as the 100% value.

Figure 9A:
FIG. 9A shows photographs of mice with HepG2 tumours treated (on the right) or not (on the left) with MVs from BM-MSCs.
Figure 9B:
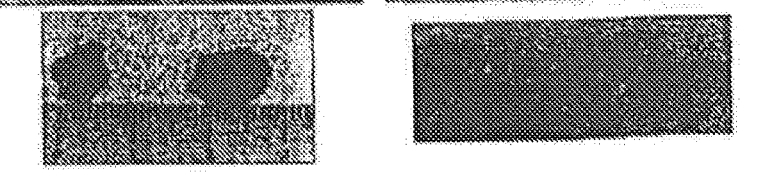
FIG. 9B shows photographs of excised HepG2 tumours treated (on the right) or not (on the left) with MVs from BM-MSCs.

FIG. 9 shows that MVs derived from BM-MSCs reduce tumor growth in vivo. A) Representative examples of mice with HepG2 tumours treated (on the right) or not (on the left) with MVs from BM-MSCs. B) Representative examples of excised HepG2 tumours treated (on the right) or not (on the left) with MVs from BM-MSCs. C) Haematoxylin and Eosin staining of HepG2 tumours treated (on the right) or not (on the left) with MVs from BM-MSCs.

Figure 10A:
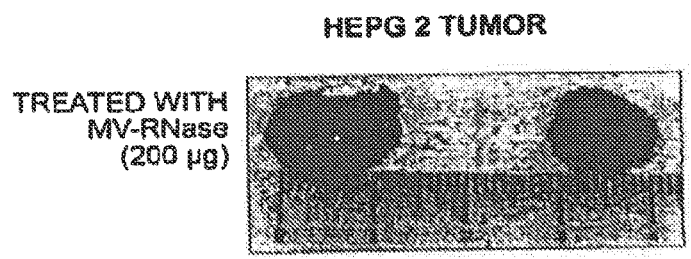
FIG. 10A shows a photograph of excised HepG2 tumours treated with MV-RNase.
Figure 10B:
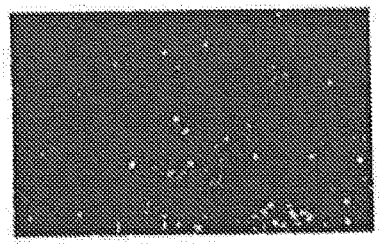
FIG. 10B shows a microscopic photograph of haematoxylin and eosin staining of cells of excised HepG2 tumours treated with MV-RNase.

FIG. 10 shows that pre-treatment of MVs with RNase abrogates the anti-tumor activity of MVs derived from BM-MSCs. A) Representative examples of excised HepG2 tumours treated with MV-RNase. B) Haematoxylin and Eosin staining of HepG2 tumours treated with MV-RNase.

Figure 11:
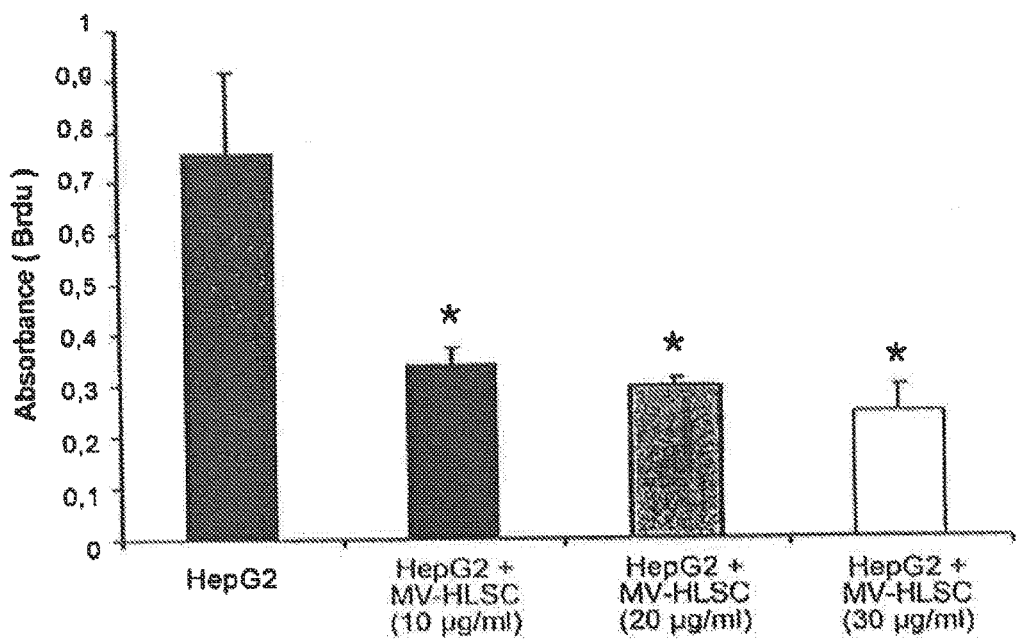
FIG. 11 is a graph showing the results of the BrdU-based proliferation assay on HepG2.

FIG. 11 is a graph showing the results of the BrdU-based proliferation assay on HepG2. HepG2 were cultured in DMEM alone or supplemented with different doses of MVs derived from HLSCs. After 3 days, HepG2 proliferation was quantified using the BrdU incorporation assay.

Figure 12:
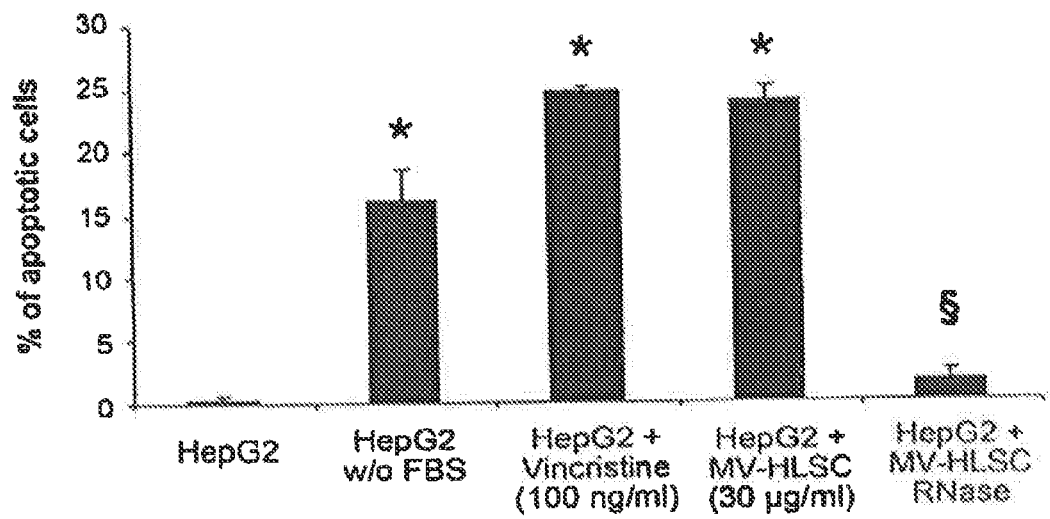
FIG. 12 is a graph showing the results of apoptosis assays on HepG2 cells.

FIG. 12 is a graph showing the results of apoptosis assays on HepG2 cells. HepG2 cells were cultured in DMEM only or with 10% FCS and supplemented with vincristine (100 ng/ml), or MV-HLSC (30 µg/ml), or MV-HLSC (pre-treated with RNase, 30 µg/ml). The analysis was performed after 24 hours.

Figure 13:
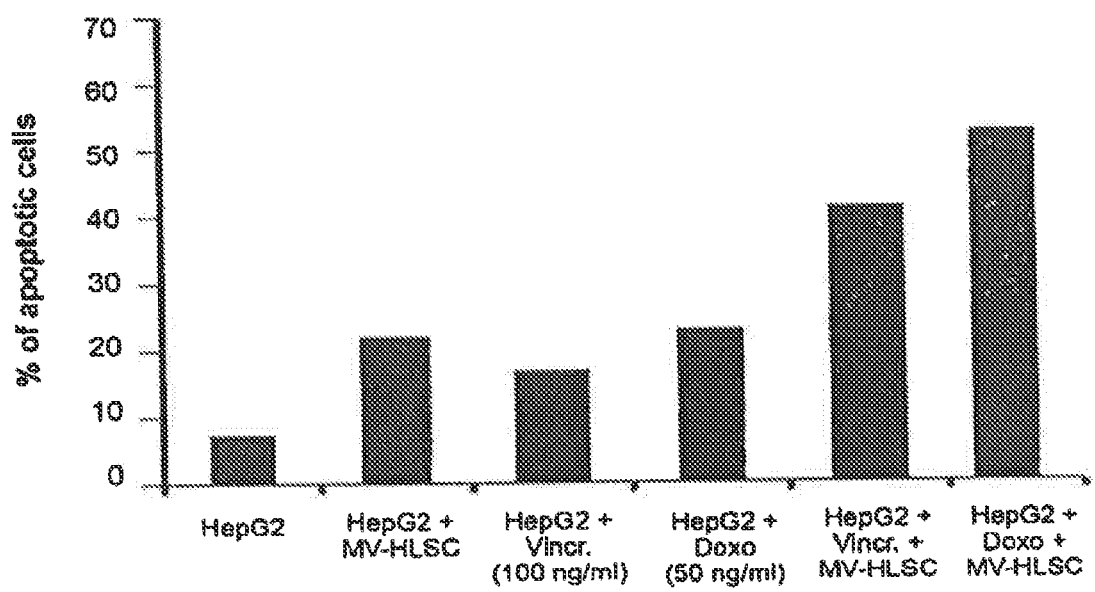
FIG. 13 is a graph showing the results of apoptosis assays on HepG2 cells under basal conditions and variously treated HepG2 cells

FIG. 13 is a graph showing the results of apoptosis assays on HepG2 cells under basal conditions or HepG2 cells treated with vincristine, doxorubicin, MV-HLSCs, or with vincristine plus MV-HLSCs and doxorubicin plus MV-HLSCs.

Figure 14:
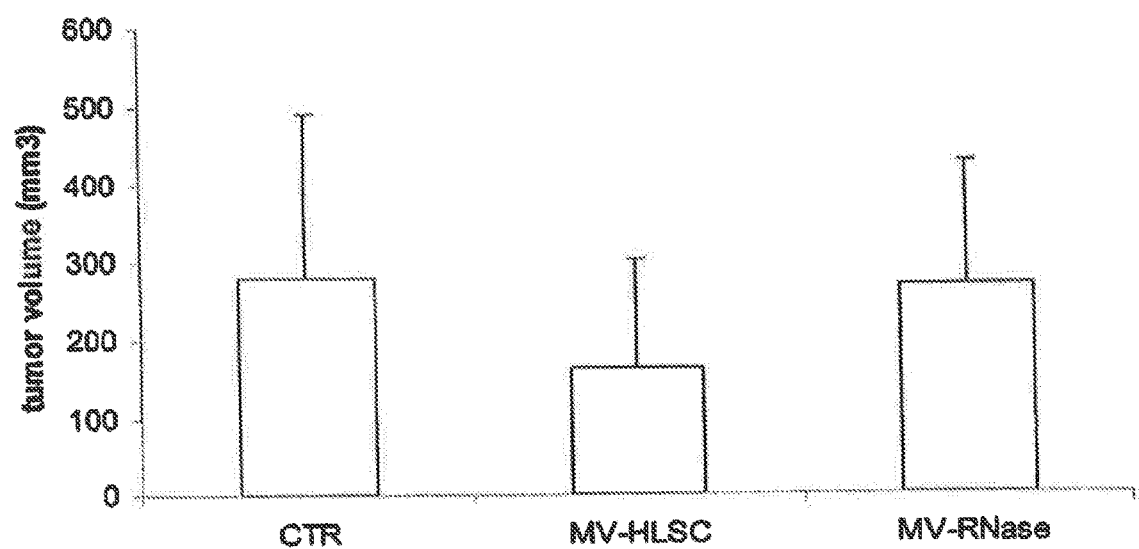
FIG. 14 is a graph showing the data obtained by measuring the tumour volume of recovered HepG2 tumors after various treatments.

FIG. 14 is a graph showing the data obtained by measuring the tumour volume of recovered HepG2 tumors after MV-HLSC (n=3), vehicle (n=2) or MV-HLSC (n=3) RNAse treated, i.t. treatment at time of mice sacrifice. Tumour volume was determined by measuring with a caliper two perpendicular diameters of the implant every week.

Figure 15:
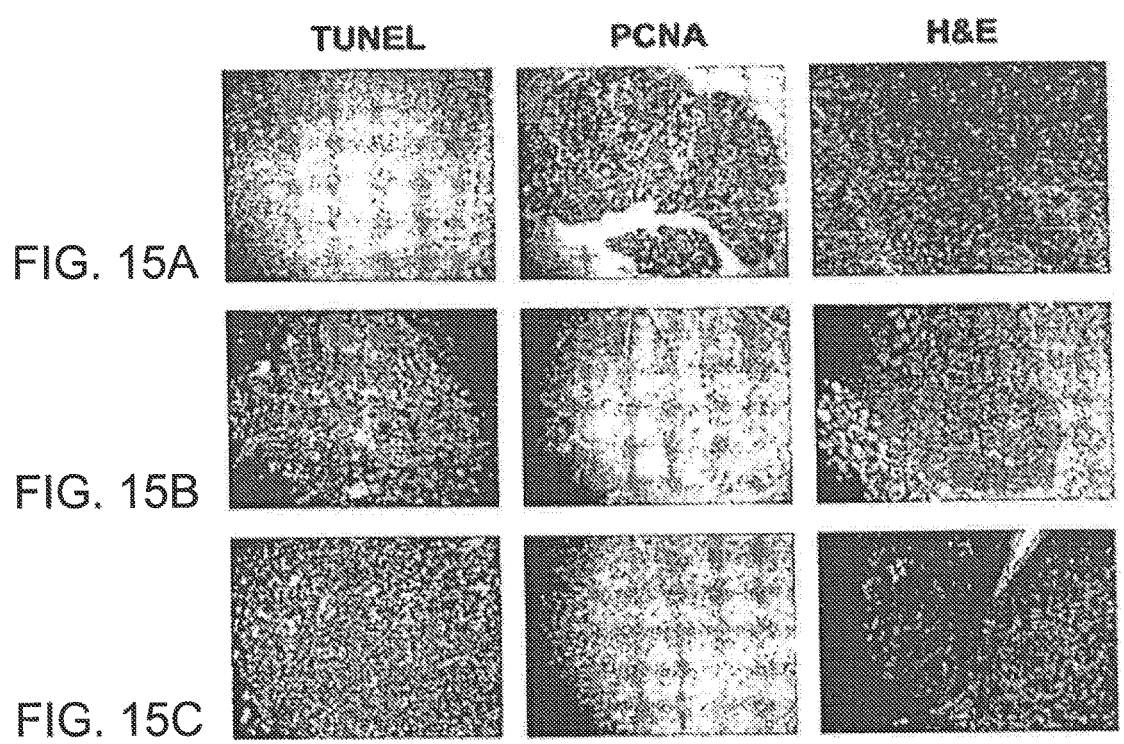
FIGS. 15A, 15B, and 15C are micrographs showing the in vive inhibition of tumour growth by HLSC-MV treatment and induced intra-tumour apoptosis.

FIG. 15 shows micrographs showing the in vivo inhibition of the tumour growth by HLSC-MV treatment and the induced intra-tumour apoptosis. A) Representative micrographs showing apoptosis. PCNA and Haematoxylin & Eosin staining of recovered HepG2 tumours after 4 weeks. B) Representative micrographs showing apoptosis, PCNA and Haematoxylin & Eosin staining of recovered HepG2 tumors from MV-treated mice. C) Representative micrographs showing apoptosis, PCNA and Haematoxylin & Eosin staining of recovered HepG2 tumors from MV-RNAse treated mice.

Figure 16:
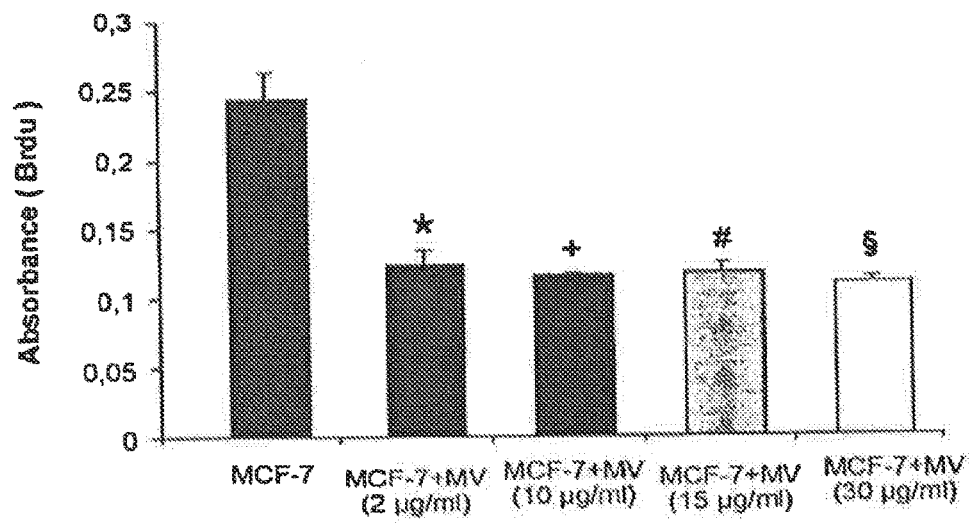
FIG. 16 is a graph showing the results of in vitro proliferation assays carried out by incubating MCF-7 cells with different concentrations of HLSC-MVs.

FIG. 16 is a graph showing the results of in vitro proliferation assays carried out by incubating MCF-7 cells with different concentrations of HLSC-MVs. Proliferation of MCF-7 cells was evaluated by BrdU incorporation assay after 48 hours of incubation with 2, 10, 15 and 30 µg/ml of MVs derived from HLSC cells. The experiment was performed in triplicate. P<0.05.

Figure 17:
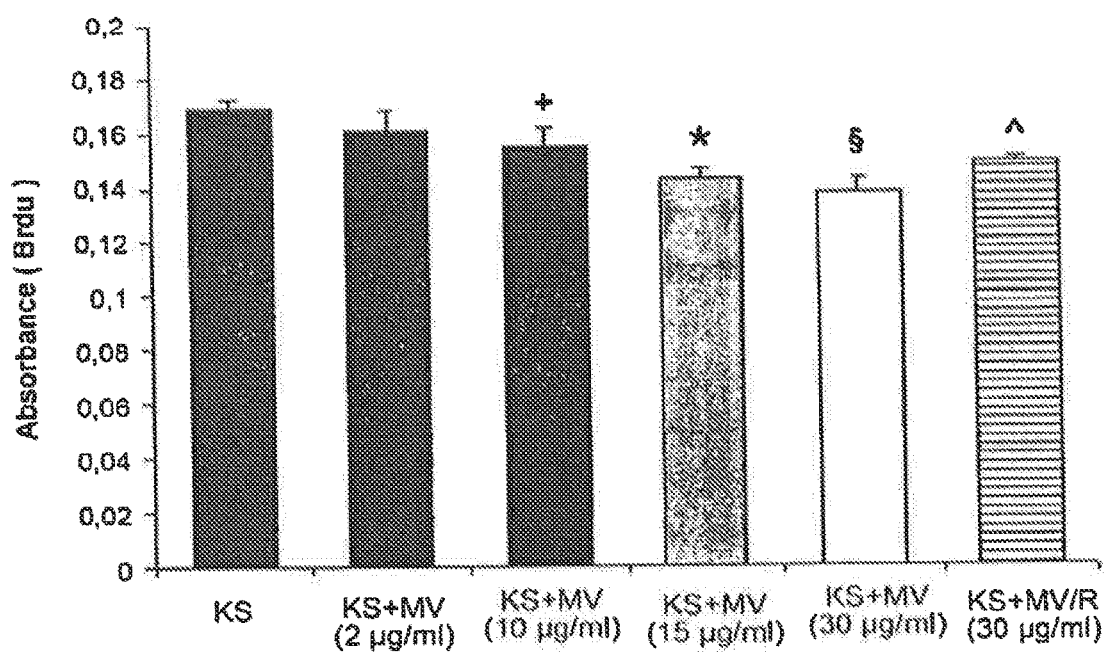
FIG. 17 is a graph showing the results of in vitro proliferation assays carried out by incubating Kaposi cells (KS) with different concentrations HLSC-MVs.

FIG. 17 is a graph showing the results of in vitro proliferation assays carried out by incubating Kaposi cells (KS)

with different concentrations HLSC-MVs. Proliferation of Kaposi cells was evaluated by BrdU incorporation assay after 48 hours of incubation with 2, 10, 15 and 30 µg/ml of MVs derived from HLSC cells. The experiment was performed in triplicate. P<0.05.

Figure 18:
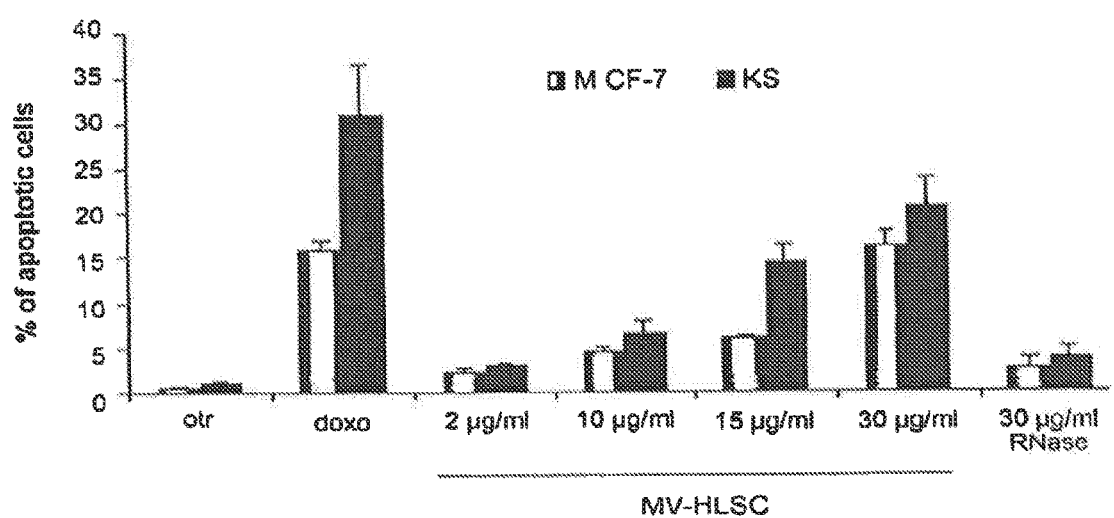
FIG. 18 is a graph showing the results of in vitro apoptosis assays carried out by incubating MCF-7 cells and Kaposi cells with HLSC-MVs.

FIG. 18 is a graph showing the results of in vitro apoptosis assays carried out by incubating MCF-7 cells and Kaposi cells with HLSC-MVs. Apoptosis was evaluated by TUNEL assay as the percentage of apoptotic cells after 48-hours of incubation with different doses of MVs (2; 10; 15; and 30 µg/ml and 30 µg/ml of RNase treated MVs). Doxorubicin were used as the positive control of apoptosis induction. In the negative control, MCF-7 cells and Kaposi cells were treated with vehicle alone. The experiment was performed in triplicate. P<0.05.

1. Microvesicles (MVs) from Mesenchymal Stem Cells (MSCs)

1.1 Isolation and Characterization of MSCs

Bone marrow cells were layered on a Ficoll gradient (density: 1022 g/ml; Sigma-Aldrich, St. Louis, Mo.) and centrifuged at 1500 rpm for 30 minutes. The mononucleated cells were cultured in the presence of Mesenchymal Stem Cells Basal Medium (MSCBM. Lonza). After 5 days of culture, the medium was changed. To expand the isolated cells, the adherent monolayer was detached by trypsin treatment for 5 minutes at 37° C. on day 15 for the first passage and every 7 days for the subsequent passages. The cells were seeded at a density of 10,000 cells/cm$^2$ and used not later than passage 6.

MSC populations from glomeruli (Gl-MSC) were obtained from the normal portion of cortex from surgically removed kidneys, as described in Bruno S et al. Isolation and characterization of resident mesenchymal stem cells in human glomeruli. Stem Cells Dev. 2009; 18:867-880. After dissection of the cortex, the glomerular suspension was collected using a standard established technique: after passing through a graded series of meshes (60 and 120 meshes), glomeruli were recovered at the top of the 120 meshes sieve. Glomeruli were then collected at the bottom of a conical tube by spontaneous precipitation (10 minutes at room temperature) and were deprived of the visceral layer of the Bowman's capsule both mechanically, by several rounds of aspiration/expulsion using a 10 ml pipette, and enzymatically, by digestion for 2 minutes with Collagenase I (Sigma, St. Louis, Mo.). Glomeruli were then collected at the bottom of a conical tube by spontaneous precipitation in order to remove cells and Bowman capsules, and were transferred to fibronectin coated T25 flasks (Falcon, BD Bioscience, Two Oak Park, Bedford, Mass.). Glomeruli were cultured in the presence of Mesenchymal Stem Cells Basal Medium (MSCBM, Lonza). Cells were left to reach confluence prior to passaging: the interval between passages varied (3-7 days) until passage 4, and from then on it was established at around 7 days.

At each passage, the cells were counted and analyzed for immunophenotype by cytofluorimetric analysis and immunofluorescence. Cytofluorimetric analysis was performed with the following antibodies, all phycoerythrin (PE) or fluorescein isothiocyanate (FITC) conjugated: anti-CD105, -CD29, -CD31, -CD146, -CD44, -CD90 (Dakocytomation, Copenhagen, Denmark): -CD73, -CD34, -CD45, -CD80, -CD86, -CD166, HLA-I (Becton Dickinson Biosciences Pharmingen, San Jose, Calif.); -CD133 (Miltenyi Biotec, Auburn): KDR (R&D Systems, Abington, U.K.); -HLA-II (Chemicon International Temecula, Calif.), -CD40 (Immunotech, Beckman Coulter), -CD154 (Serotec, Raleigh, N.C. USA) monoclonal antibodies. Mouse IgG isotypic controls were from Dakocytomation. All incubations were performed in 100 µl of phosphate buffered saline (PBS) containing 0.1% bovine serum albumin and 0.1% sodium azide, at 4° C. For each sample, 10,000 cells were analysed on FACSCalibur cytometer (BD Biosciences Pharmingen). Gating was constructed based on negative controls and compensation controls were included in all analyses performed. Population percentages and numbers were generated for gated populations from each experiment using Cell Quest software (BD Biosciences Pharmingen).

Indirect immunofluorescence was performed on MSCs cultured on chamber slides (Nalgen Nunc International, Rochester, N.Y., USA), fixed in 4% paraformaldehyde containing 2% sucrose and, if required, permeabilized with Hepes-Triton X 100 buffer (Sigma, St. Louis, Mo.). The following antibodies were used: mouse monoclonal anti-vimentin (Sigma) and rabbit policlonal anti-von Willebrand factor (Dakocytomation). Omission of the primary antibodies or substitution with non immune rabbit or mouse IgG were used as controls where appropriated. Alexa Fluor 488 anti-rabbit and anti-mouse Texas Red (Molecular Probes. Leiden, The Netherlands) were used as secondary Abs. Confocal microscopy analysis was performed using a Zeiss LSM 5 Pascal Model Confocal Microscope (Carl Zeiss International, Germany). Hoechst 33258 dye (Sigma) was added for nuclear staining.

BM-MSC and GL-MSC preparations did not express hematopoietic markers such as CD45, CD14 and CD34. They neither expressed the co-stimulatory molecules (CD80, CD86 and CD40) and the endothelial markers (CD31, von Willebrand Factor, KDR). All the cell preparations at different passages of culture expressed the typical MSC markers: CD105, CD73, CD44, CD90, CD166 and CD146. They also expressed HLA class I.

The adipogenic, osteogenic and chondrogenic differentiation abilities of MSC were determined as described in Pittenger M F, Martin B J. Mesenchymal stem cells and their potential as cardiac therapeutics. Circ. Res 2004; 95:9-20. In brief, MSCs were cultured with Adipogenic Medium (Lonza) for 3 weeks. To evaluate the differentiation, the cells were fixed with 4% paraformaldehyde for 20 minutes at room temperature and stained with 0.5% Oil Red O (Sigma) in methanol (Sigma) for 20 minutes at room temperature.

Osteogenic differentiation was assessed by culturing MSCs in Osteogenic Medium (Lonza). The medium was changed twice per week for 3 weeks. To evaluate the differentiation, cells were fixed with 4% paraformaldehyde for 20 minutes and stained with Alizarin Red, pH 4.1 (Lonza) for 20 minutes at room temperature.

For chondrogenic differentiation, 2.5×10$^5$ MSCs were centrifuged in a 15-ml conical polypropylene tube (Falcon BD Bioscience) at 150 g for 5 minutes and washed twice with DMEM. The pellets were cultured in Chondrogenic medium (Lonza) supplemented with 10 ng/ml of Transforming Growth Factor 33 (Lonza). The medium was changed every 3 days for 28 days. Pellets were fixed in 4% paraformaldehyde overnight, and the paraffin-embedded sections were stained for glycosaminoglycans using 0.1% safranin O (Sigma) and for sulfated proteoglycans using 1% alcian blue.

1.2 Isolation and Characterization of MVs Derived from MSCs

The microvesicles (MVs) were obtained from supernatants of BM-MSCs or GL-MSCs obtained as describe above cultured in RPMI deprived of FCS and supplemented with 0.5% of BSA (Sigma). After centrifugation at 2,000 g for 20 minutes to remove debris, cell-free supernatants were centrifuged at 100,000 g (Beckman Coulter Optima L-90K ultracentrifuge) for 1 hour at 4° C., washed in serum-free medium 199 containing N-2-hydroxyethylpiperazine-N'-2-ethanesulfonic acid (HEPES) 25 mM (Sigma) and subjected to a second ultracentrifugation under the same conditions. Endotoxin contamination of MVs was excluded by Limulus test according to the manufacturer's instructions (Charles River Laboratories, Inc., Wilmington, Mass., USA) and MVs were stored at −80° C.

In selected experiments, MVs were treated with 1 U/ml RNase (Ambion Inc., Austin, Tex. USA) for 1 hour at 37° C., the reaction was stopped by addition of 10 U/ml RNase inhibitor (Ambion Inc.) and MVs were washed by ultracentrifugation.

1.3 In Vitro Experiments Performed with MVs Derived from MSCs

Cancer Cell Lines Culture.

Human liver cancer cell line (HepG2), human breast adenocarcinoma cell line (MCF-7) and human ovarian cancer cell line (SKOV-3) were cultured in low glucose DMEM (Euroclone) containing 10% of Fetal Calf Serum (FCS, Euroclone), 100 U/ml penicillin, 100 mg/ml streptomycin and 1% glutamine (all from Sigma) and maintained in an incubator with a humidified atmosphere of 5% $CO_2$ at 37° C. A primary culture of Kaposi's sarcoma cells (KS cells) was obtained from a cutaneous lesion of a patient bearing renal allograft under immunosuppressive therapy and cultured in RPMI 1640 medium supplemented with 10% of FCS, 100 gig/ml penicillin, and 100 µg/ml streptomycin.

Tumor Endothelial Cells (TECs): Isolation and Culture.

TECs were isolated from specimens of clear-cell type renal cell carcinomas using anti-CD105 Ab coupled to magnetic beads by magnetic cell sorting using the MACS system (Miltenyi Biotec, Auburn, Calif., USA). TEC cell lines were established and maintained in culture in endothelial basal complete medium (EBM) supplemented with epidermal growth factor (10 ng/ml), hydrocortisone (1 mg/ml), bovine brain extract (all from Lonza) and 10% FCS. TECs were characterized as endothelial cells by morphology, positive staining for vWF antigen, CD105, CD146, and vascular endothelial-cadherin and negative staining for cytokeratin and desmin (Bussolati B et al. Altered angiogenesis and survival in endothelial cells derived from renal carcinoma. FASEB J 2003; 17:1159-1161).

Humbelical Vein Endothelial Cells (HUVECs): Isolation and Culture.

Human umbilical vein endothelial cells (HUVECs) were obtained from the umbilical vein, as described previously (Bussolati B et al. Vascular endothelial growth factor receptor-1 modulates vascular endothelial growth factor-mediated angiogenesis via nitric oxide. Am J Pathol. 2001 September; 159(3):993-1008) and maintained in EBM and 10% FCS. Experiments were performed on second or third passage HUVECs.

Cell Proliferation.

HepG2. MCF-7, SKOV-3, KS cells or HUVECs were seeded at 2,000 or 4,000 cells/well into 96-well plates in DMEM (Sigma) deprived of FCS with different concentrations of microvesicles pre-treated or not pre-treated with RNase. DNA synthesis was detected as incorporation of 5-bromo-2'-deoxy-uridine (BrdU) into the cellular DNA after 48 hours of culture. Cells were then fixed with 0.5 M ethanol/HCl and incubated with nuclease to digest the DNA. BrdU incorporation into the DNA was detected using an anti-BrdU peroxidase-conjugated mAb and visualized with a soluble chromogenic substrate (Roche Applied Science. Mannheim, Germany). Optical density was measured with an ELISA reader at 405 nm.

Cell Cycle Analysis.

Human cancer cell lines were stimulated for 24 hours with 30 µg/ml of different preparations of MVs, detached by trypsin and fixed in cold 80% ethanol. Cells were maintained for at least 24 hours at −20° C. and then washed in PBS. Then, the cells were incubated for 1 hour at room temperature with propidium iodide (50 µg/ml) (Sigma) to stain the DNA in a solution containing RNase (200 µg/ml) (Sigma) and 0.5% of Nonidet P40 (Sigma). For each sample, 50,000 cells were analysed on FACSCalibur cytometer (BD Biosciences Pharmingen).

Apoptotic Assay.

HepG2, MCF-7, SKOV-3, KS cells, HUVECs or TECs were seeded at 8,000 cells/well into 96-well plated in DMEM (Sigma) with 10% FCS and in the presence of doxorubicin (100 ng/ml, Sigma) or different concentrations of MVs (10 and 30 µg/ml) pre-treated or not with RNase. Apoptosis was assessed by TUNEL assay (ApopTag Oncor, Gaithersburg, Md., USA). After 24 or 48 hours of treatment, the cells were washed with PBS, fixed in 1% paraformaldehyde pH 7.4 for 15 minutes at 4° C., washed twice in PBS and then post-fixed in pre-cooled ethanol-acetic acid 2:1 for 5 minutes at −20° C. The samples were treated with the enzyme terminal deoxynucleotidyl transferase (TdT). The cells were then treated with heated anti-digoxigenin conjugate with fluorescein and incubated for 30 minutes at room temperature. The samples were mounted in medium containing 1 µg/ml of propidium iodide and the cells analyzed by immunofluorescence. The results are expressed as the percentage of green fluorescence emitting cells (apoptotic cells) versus red fluorescence emitting cells (total cells).

Angiogenesis In Vitro.

24-well plates were coated with growth factor-reduced Matrigel (BD Biosciences) at 4° C. and incubated for 30 minutes at 37° C., 5% $CO_2$, in a humidified atmosphere. HUVECs or TECs were seeded on the Matrigel-coated wells in RPMI or EBM with 5% FCS at the density of $5 \times 10^4$ cells/well, in the presence or in the absence of different concentrations of MVs treated or not treated with RNase. After 6 hours of incubation, the cells were observed under a Nikon inverted microscope (Nikon) and the experimental results were recorded. The results were expressed as the mean of the tube length, measured with the MicroImage analysis system (Cast Imaging), expressed in arbitrary units and evaluated in 5 different fields at a magnification of 20× in duplicate wells from 3 different experiments.

Statistical Analysis.

All data from different experimental procedures are expressed as the mean±SD. Statistical analysis was performed by ANOVA with Newmann-Keuls multi-comparison test where appropriate.

1.4 In Vitro Results 1.4.1 In Vitro Biological Effects of MVs Derived from BM-MSCs and GL-MSCs on Tumour Cell Lines The anti-tumour activity of MVs derived from human BM-MSCs, was assessed in vitro by measuring their ability to inhibit proliferation and to induce apoptosis on HepG2, MCF-7, SKOV-3 and KS cell lines.

FIG. 1 shows that incubation of HepG2 cells (FIG. 1A) and KS cells (FIG. 1B) with different doses of MVs for 48 hours significantly inhibited proliferation compared to control cells incubated with vehicle alone.

Figure 2A:
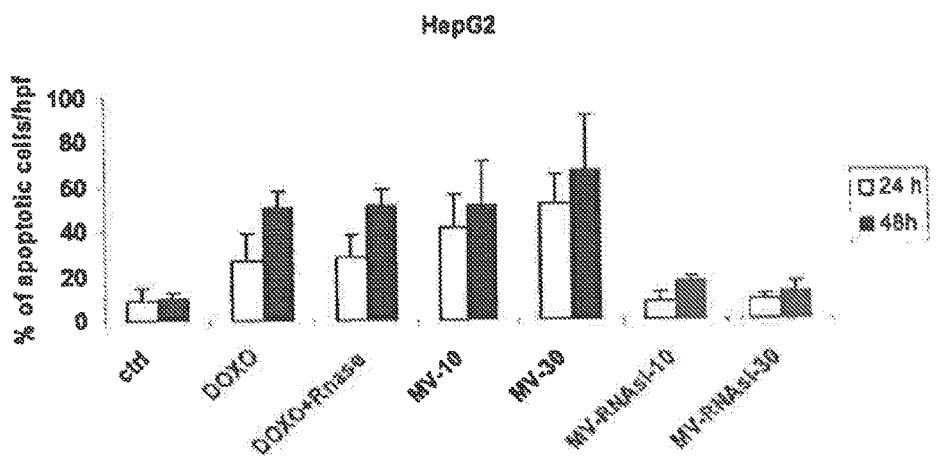
FIGS. 2 A and B graphically show the incubation results of HepG2 and KS cells with MVs.
Figure 2B:
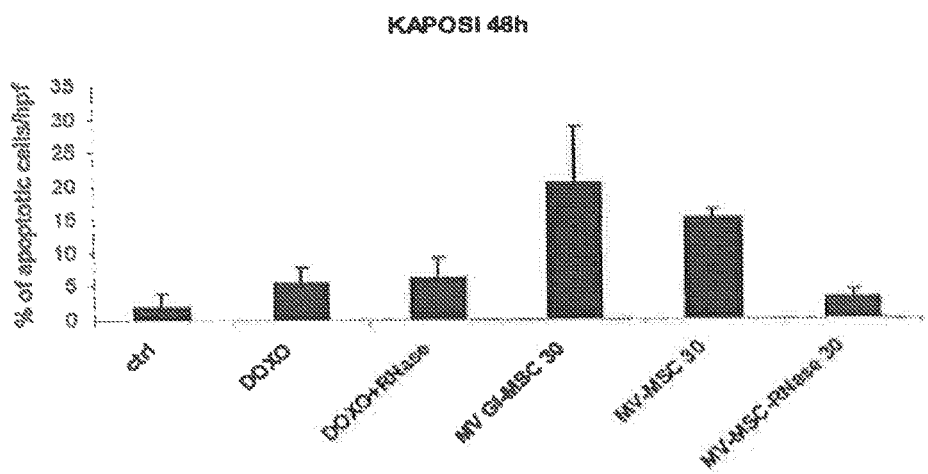

FIG. 2 shows that incubation of HepG2 cells (FIG. 2A) and KS cells (FIG. 2B) with MVs for 24 and 48 hours significantly promoted apoptosis compared to control cells incubated with vehicle alone and in the same way of doxorubicin stimulation.

When MVs were incubated with RNase to induce complete degradation of the RNA shuttled by MVs, the anti-proliferation and pro-apoptotic effects elicited by MVs on HepG2 and KS cells were reduced (FIGS. 1 and 2). RNase treatment of MVs did not interfere per se with cancer cell line apoptosis induced by doxorubicin (FIG. 2).

On the contrary, incubation of MCF-7 cells and SKOV-3 cells with 30 µg/ml of MVs from BM-MSCs for 48 hours significantly inhibited proliferation compared to control cells incubated with vehicle alone (FIGS. 3A and 3B), but did not promote apoptosis. In these two tumour cell lines the inventors have also studied cell cycle with the propidium iodide staining technique, in order to evaluate the percentage of cells in the G0/G1 phase in comparison with the cells in the S and G2 phases. The inventors have observed that MVs from BM-MSCs induced an increase of cells in the G0/G1 phase, especially in SKOV-3 cells (FIG. 4), which may explain the inhibition of proliferation observed with BrdU incorporation.

The inventors have also tested the effects of MVs derived from Gl-MSCs on the proliferation and apoptosis of tumor cell lines. Gl-MSCs did not affect proliferation and apoptosis of the HepG2 cell line. On the contrary, MVs derived from Gl-MSCs inhibited proliferation and induced apoptosis of KS cells (FIGS. 1 and 2). Moreover, incubation of MCF-7 and SKOV-3 cells with 30 µg/ml of MVs derived from Gl-MSCs for 48 hours inhibited proliferation compared to control cells incubated with vehicle alone (FIG. 3), but did not promote apoptosis.

1.4.2 MVs Derived from Human Fibroblasts

MVs derived from human fibroblasts did not inhibit proliferation and did not induce apoptosis of different cancer cell lines (data not shown).

1.4.3 In Vitro Effects of MVs Derived from BM-MSCs on Endothelial Cells

The inventors have also studied the in vitro effects of MVs derived from BM-MSCs on the proliferation, apoptosis and capillary-like formation of HUVECs and tumour endothelial cells (TECs).

MV-treatment did not affect the proliferation (data not shown) and the capillary-like formation ability of HUVECs (FIG. 5A). In addition, incubation of HUVECs with different doses of MVs for 48 hours did not induce apoptosis (FIG. 6).

In contrast, the incubation of TECs with different doses of MVs for 48 hours, significantly inhibited proliferation (FIG. 7) and promoted apoptosis (FIG. 6) compared to the control cells incubated with vehicle alone. Proliferation of TECs was evaluated by BrdU incorporation assay after 48 hours of incubation with different doses of MVs (10 and 30 µg/ml) from BM-MSCs pre-treated or not with RNase. The results in FIG. 7 are expressed as the mean±SD of 2 experiments.

When MVs were incubated with RNase, the apoptotic effect elicited by MVs on TECs was significantly reduced. Incubation of TECs seeded on Matrigel with different doses of MVs significantly inhibited the ability of TECs to form capillary-like structures in vitro. Pre-treatment of MVs with RNase abrogated the inhibitory effect on MVs on tubule formation (FIG. 5B).

1.5 In Vivo Experiments with MVs Derived from MSCs Tumor Formation.

$3 \times 10^6$ HepG2 cells were collected and implanted subcutaneously into SCID mice (Charles River, Jackson Laboratories, Bar Harbor, Me.). Cultured cells, harvested using trypsin-EDTA, were washed with PBS, counted in a microcytometer chamber and resuspended in 100 µl of DMEM and 100 µl of Matrigel Matrix (Becton Dickinson). The cells were chilled on ice, and injected subcutaneously into the left back of SCID mice via a 26-gauge needle using a 1-ml syringe. The animals were monitored for activity and physical conditions every day, and the determination of body weight and measurement of tumour mass was made every 3 days. Tumour mass was determined by calliper measurement in two perpendicular diameters of the implant and calculated using the formula $½ a \times b^2$, where a is the long diameter and b is the short diameter (Hou J et al. Experimental therapy of hepatoma with artemisin and its derivatives: in vitro and in vivo activity, chemosensitization and mechanism of action. Clin Cancer Research. 2008; 14:5519-5530)). After 1 week, when the implanted tumours reached the volume of approximately 15 mm$^3$, the inventors started the weekly intra-tumour injection of MVs. The first treatment was with 100 µg of MVs (treated or not with RNase) for a maximum volume of 20 µl; the subsequent intra-tumour injections were of 50 µg of MVs (treated or not with RNase), for a maximum of 20 µl. In control mice, the inventors injected intra-tumour the same volume of vehicle alone. Mice were randomized into three treatment groups: a) the group intra-tumor injected with of MVs (n=8); b) the group intra-tumor injected with MVs treated with RNase (n=8); and c) the control group injected with the same volume of vehicle alone (n=5). After three weeks from Matrigel injection, mice were sacrificed and tumours recovered and processed for histology.

1.6 In Vivo Results 1.6.1 In Vivo Biological Effects of MVs Derived from BM-MSCs on HEPG2 Tumor Growth Tumor formation and growth are inhibited by MVs derived form BM-MSCs in SCID mice. To determine the effect of MVs derived from BM-MSCs on tumor formation and growth in vivo, SCID mice were injected subcutaneously with HepG2 in the presence of Matrigel. One week after the injection, when the volume of tumours was about 15 mm$^3$, the inventors started to weekly inject the mice intra-tumour with MVs (treated or not with RNase), with a maximum volume of 20 µl. The first treatment was with 100 µg of MVs; the subsequent intra-tumour injections were with 50 µg of MVs. In control mice, the inventors injected inject 20 µl of vehicle alone intra-tumour.

Figure 9C:
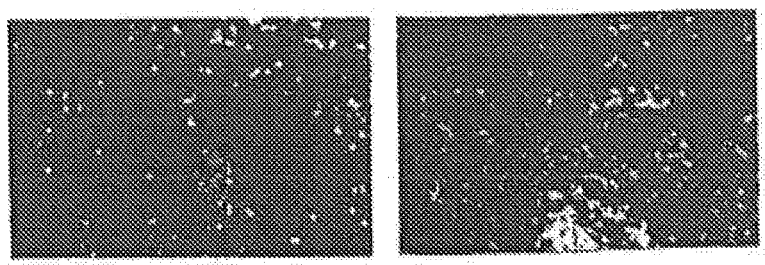
FIG. 9C shows microscopic photographs of haematoxylin and eosin staining of cells of excised HepG2 tumours treated (on the right) or not (on the left) with MVs from BM-MSCs.

After three weeks from Matrigel injection, all tumours were recovered and analyzed. In the HepG2 xenograft model, MV intra-tumor injection showed a inhibitor effect on tumor growth (FIG. 8). Tumor size and volume were significantly smaller in SCID mice treated with MVs (FIGS. 9 A and B) and histological analyses showed areas of necrosis in HepG2 tumours treated with MVs (FIG. 9C). Tumours injected with MVs pre-treated with RNase did not differ in size and histology from control tumours (FIGS. 10 A and B).

2. Microvesicles (MVs) from Liver Stem Cells 2.1 Isolation and Characterization of Adult Human Liver Stem Cells (HLSCs)

HLSCs were isolated from human cryopreserved normal hepatocytes obtained from Cambrex Bio Science Verviers S.p.r.l. (Verviers, Belgium) cultured in minimum essential medium/endothelial cell basal medium-1 (α-MEM/EBM) (3:1) (Gibco/Cambrex) supplemented with L-glutamine (5 mM), Hepes (12 mM, pH 7.4), penicillin (50 IU/ml), streptomycin (50 µg/ml) (all from Sigma, St. Louis), FCS (10%). The expanded cells were transferred to a T-75 flask and analyzed when they approached confluence.

The hepatoma cell line HepG2 were cultured in Dulbecco's modified Eagle's medium (DMEM) (low glucose) containing 10% fetal bovine serum (FBS).

2.2 Isolation of MVs Derived from HLSCs

MVs were obtained from supernatants of HLSCs cultured in MEM-alpha supplemented with 2% of Fetal Bovine Serum (FBS). The viability of cells incubated overnight without serum was detected by trypan blue exclusion. After centrifugation at 2000 g for 20 minutes to remove debris, cell-free supernatants were centrifuged at 100,000 g (Beckman Coulter Optima L-90K ultracentrifuge) for 1 h at 4° C., washed in serum-free medium 199 containing N-2-hydroxyethylpiperazine-N'-2-ethanesulfonic acid (HEPES) 25 mM (Sigma) and subjected to a second ultracentrifugation under the same conditions. To trace, in vitro and in vivo, MVs by fluorescence microscopy or FACS analysis, MVs from stem cells were labelled with the red fluorescence aliphatic chromophore intercalating into lipid bilayers PKH26 dye (Sigma). After labelling, MVs were washed and ultracentrifuged at 100,000 g for 1 h at 4° C. MV pellets were suspended in medium 199, and the protein content was quantified by the Bradford method (BioRad, Hercules, Calif.). Endotoxin contamination of MVs was excluded by Limulus testing according to the manufacturer's instructions (Charles River Laboratories, Inc., Wilmington, Mass.), and MVs were stored at −80° C. The morphologic analysis performed on MV suspension after staining with propidium iodide did not show the presence of apoptotic bodies.

In selected experiments, MVs from HLSCs were treated with 1 U/ml RNase (Ambion Inc., Austin, Tex.) for 1 h at 37° C., the reaction was stopped by the addition of 10 U/ml RNase inhibitor (Ambion Inc.) and MVs were washed by ultracentrifugation. The effectiveness of RNase treatment was evaluated after RNA extraction using TRIZOL reagent (Invitrogen, Carlsbad, Calif.) by spectrophotometer analysis of total extracted RNA (untreated: 1.3±0.2 µg RNA/mg protein MV; RNase treated: <0.2 µg RNA/mg protein MV). In addition, RNA extracted from RNase-treated and untreated MVs was labelled by oligo dT driven retrotranscription and analyzed on 0.6% agarose gel to show the complete degradation of RNA by RNase treatment. As a control, MVs were treated with 1 U/ml DNase (Ambion Inc.) for 1 h at 37° C.

2.3 In Vitro Experiments Performed with MVs Isolated from HLSCs

Proliferation Assay.

DNA synthesis was detected as the incorporation of 5-bromo-2-deoxyuridine (BrdU) into the cellular DNA using an enzyme-linked immunosorbent assay kit (Chemicon, Temecula, Calif.) according to the manufacturer's instructions. Briefly, after washing, the cells were incubated with 10 mol/l BrdU for 6 to 12 hours at 37° C., 5% $CO_2$, in a humidified atmosphere, fixed with 0.5 mol/L ethanol/HCl and incubated with nuclease to digest DNA. BrdU incorporated into the DNA was detected using an anti-BrdU peroxidase-conjugated monoclonal antibody and visualized with a soluble chromogenic substrate. Optical density was measured with an enzyme-linked immunosorbent assay reader at 405 nm.

Apoptosis Assay.

Apoptosis was evaluated using the terminal dUTP nick-end labeling assay (ApoTag; Oncor, Gaithersburg, Md.). Cells (8×10/well) were cultured in 96-well plate, suspended in phosphate-buffered saline (PBS) and fixed in 1% paraformaldehyde in PBS, pH 7.4, for 15 minutes at 4° C. followed by pre-cooled ethanol/acetic acid (2:1) for 5 minutes at −20° C. Cells were treated with terminal deoxynucleotide transferase enzyme and incubated in a humidified chamber for 1 hour at 37° C. and then treated with warmed fluorescein isothiocyanate-conjugated antidigoxigenin for 30 minutes at room temperature. After washing, samples were mounted in a medium containing 1 g/ml of propidium iodide and the cells were analyzed by immunofluorescence.

Statistical Analysis.

All data of different experimental procedures are expressed as average±SD. Statistical analysis was performed by ANOVA with Newmann-Keuls multi-comparison test where appropriate.

2.4 In Vitro Results 2.4.1 Effects of MVs Derived from HLSCs on the Proliferation of the HepG2 Hepatoma Cell Line The inventors evaluated the effects of MVs derived from HLSCs on HepG2 proliferation. Briefly, HepG2 cells were incubated with different doses (10, 20 and 30 µg/ml) of HLSC-derived MVs as such or treated with RNase for 3 days. At the end of incubation, HepG2 cultures were counted or fixed in 0.5 M ethanol/HCl and incubated with nuclease to digest the DNA. BrdU incorporated into the DNA was detected using an anti-BrdU peroxidase-conjugated mAb and visualized with a soluble chromogenic substrate. Optical density was measured with an ELISA reader at 405 nm. As shown in FIG. 11, MVs derived from HLSCs are able to inhibit significantly HepG2 proliferation. This also applies to RNase treated MVs.

2.4.2 Effects of MVs Derived from HLSCs on the Apoptosis of the HepG2 Hepatoma Cell Line The ability of HLSC-derived MVs to induce apoptosis on HepG2 was evaluated. Briefly, HepG2 were seeded at a density of 8,000 cells/well into 96-well plates in DMEM with 10% FCS and apoptosis was induced by culture in the absence of FCS, by treatment with vincristine (100 ng/ml), or doxorubicin (50 ng/ml), two mitotic inhibitors used in cancer chemotherapy, or by MV treatment (30 µg/ml). As a control, MVs were also treated with 1 U/ml RNase18 (Ambion, Austin, Tex.) for 1 hour at 37° C. to assess whether the contribution to the inhibition of cancer cells growth is dependent to an horizontal transfer of mRNA delivered by MV to the cancer cells. Apoptosis was evaluated using the TUNEL assay analysis at 24 and 72 hours. As shown in FIG. 12, MVs derived from HLSCs were able to induce HepG2 apoptosis comparable to that induced by vincristine. On the contrary, the RNase treatment failed to induce apoptosis. In addition, treatment of HepG2 with vincristine plus MV-HLSCs or doxorubicin plus MV-HLSCs results in an additive effect as shown in FIG. 13.

2.5 In Vivo Experiments Performed with MVs Isolated from HLSCs

Cell Culture.

Human hepatoma cells HepG2, were cultured in DMEM supplemented with 10% fetal bovine serum, 100 µg/ml penicillin, and 100 µg/ml streptomycin and maintained in an incubator with a humidified atmosphere of 5% $CO_2$ at 37° C.

Human liver stem cells (HLSCs) were cultured in α-MEM/EBM (3:1), supplemented with 10% fetal bovine serum, 100 µg/ml penicillin, and 100 µg/ml streptomycin. EBM was reconstituted with hEGF (human Epithelial Growth Factor), Hydrocortisone, GA (gentamicin), BBE (Brain Bovine Extract).

Isolation of Microvesicles (MVs) from HLSCs.

MVs were obtained from supernatants of HLSCs cultured in α-MEM medium supplemented with 2% fetal bovine serum. After centrifugation at 2,000 g for 20 minutes to remove debris, cell-free supernatants were centrifuged at 100,000 g for 1 hour at 4° C., washed in serum-free medium 199 containing N-2-hydroxyethylpiperazine-N'-2-ethanesulfonic acid (HEPES) 25 mM and submitted to a second ultracentrifugation under the same conditions. MV pellets were suspended in medium 199 in 0.1% of DMSO and the protein content was quantified using the Bradford method.

Experimental Design.

Male 4- to 5-mo-old SCID mice were obtained from Charles River laboratories. All mice were housed in a clean facility and held for 1 week to acclimatize. On day 0, two injections of 3×10⁶ HepG2 tumour cells resuspended in serum-free DMEM with Matrigel basement membrane matrix at a 1:1 ratio were applied. Cell suspension was injected in a total volume of 0.2 ml into the left inguinal area of the SCID mice. All mice were randomized into three treatment groups: 20 µl of intratumoral (i.t.) MV injection (n=3), 20 µl of i.t. PBS injection (n=2) and 20 µl of i.t. MV-RNase treated injection (n=3). On day 7 post-tumour cell transplantation treatment started. Tumours became palpable as from day 7; 50 or 100 µg of MV, suspended in M199 supplemented with 0.1% of DMSO, were injected 7, 12, 14 and 18 days after tumour transplantation. Treatment started when tumours rinse the volume of approximately 15 mm3. The animals were monitored for activity and physical condition every day, and the determination of body weight and measurement of tumour mass were done every 3 days.

Tumours were Measured with Callipers.

Tumour mass was determined by calliper, measurement in two perpendicular diameters of the implant and calculated using the formula $\frac{1}{2}a \times b^2$, where a is the long diameter and b is the short diameter. The animals were sacrificed on day 28, and tumours were collected for further analysis.

Morphological Studies.

Tumours were fixed in 10%/o buffered neutral formalin, routinely processed, embedded in paraffin, sectioned at 5 µm, and stained with H&E for microscopic examination. Immunohistochemistry for detection of proliferation was performed using the anti-PCNA monoclonal antibody. Sections were blocked and labeled with anti-mouse HRP secondary antibody (1:300 dilution). Omission of the primary antibodies or substitution with non immune mouse IgG was used as controls. Apoptosis was evaluated in paraffin-embedded tumor sections by TUNEL. Ten non consecutive sections were counted for apoptotic-positive tumor cells at 630× magnification. Hoechst 33258 dye was added for nuclear staining.

Statistical Analysis.

All data of different experimental procedures are expressed as mean±SD. Statistical analysis was performed by ANOVA with Newmann-Keuls multi-comparison test where appropriate.

2.6 In Vivo Results 2.6.1 Tumour Growth and Proliferation were Inhibited by MVs Derived Form HLSCs in a Hepatoma Xenograft Model in SCID Mice To determine the effect of MVs derived from HLSC son tumour growth in vivo, SCID mice were subcutaneously transplanted with the human hepatocarcinoma cell line HepG2. One and two weeks after the injection of HepG2, when the volume of tumours was about 15 mm³, mice were treated with intra-tumour injection of MVs (50 or 100 µg), for a maximum of 20 µl of volume. In control mice, tumour were injected with 20 µl of vehicle alone. After three and four weeks from HepG2 injection, all tumours were recovered and analyzed. In this xenograft model, intra-tumor injection of MVs (FIG. 14) showed a inhibitor effect on tumour growth. In addition, histological analyses showed areas of necrosis in tumours treated with MVs (FIG. 15 B) and anti-proliferative effect was observed using PCNA staining (FIG. 15 B).

2.6.2 Induction of Apoptosis by MVs Derived Form HLSCs in a Hepatoma Xenograft Model in SCID Mice To determine the effect in intra-tumour apoptosis, paraffin sections from tumours treated with MVs were analysed by TUNEL. MV treatment induced apoptosis compared to tumours treated with vehicle alone (FIG. 15 A).

2.7 In Vitro Biological Effect of MVs Derived from HLSCs on MCF-7 Breast Adenocarcinoma and Kaposi's Sarcoma (KS) Cells 2.7.1 Materials and Methods Cell Culture.

Human non oval liver stem cells (HLSC) were cultured in α-MEM/EBM (3:1), supplemented with 10% fetal bovine serum, 100 µg/ml penicillin and 100 µg/ml streptomycin. EBM was reconstituted with hEGF (human Epithelial Growth Factor), Hydrocortisone, GA (gentamicin), BBE (Brain Bovine Extract).

MCF-7 breast adenocarcinoma cell lines were obtained from American Type Culture Collection (Manassas, Va.) and were cultured in DMEM supplemented with 10% of FCS, 100 µg/ml penicillin and 100 µg/ml streptomycin and maintained in an incubator with a humidified atmosphere of 5% $CO_2$ at 37° C.

A primary culture of Kaposi's sarcoma cells (KS cells) was obtained from a cutaneous lesion of a patient bearing renal allograft under immunosuppressive therapy and was cultured in RPMI 1640 medium supplemented with 10% of FCS, 100 µg/ml penicillin and 100 µg/ml streptomycin.

Isolation of MVs.

MVs were obtained from supernatants of HLSCs cultured in MEM-alpha supplemented with 2% of Fetal Bovine Serum (FBS) for 18 hours. In selected experiments, MVs were collected in the absence of FBS. The viability of cells incubated overnight at 2% of FBS and without serum was detected by trypan blue exclusion (more than 90%, data not shown). After centrifugation at 2,000 g for 20 minutes to remove debris, cell-free supernatants were centrifuged at 100,000 g (Beckman Coulter Optima L-90K ultracentrifuge) for 1 h at 4° C. washed in serum-free medium 199 containing N-2-hydroxyethylpiperazine-N'-2-ethanesulfonic acid (HEPES) 25 mM and subjected to a second ultracentrifugation under the same conditions. MV pellets were suspended in medium 199, and the protein content was measured with the Bradford method. MVs were stored at −80° C. The morphologic analysis performed on a MVs suspension after staining with propidium iodide did not show the presence of apoptotic bodies.

RNase Treatment.

In selected experiments, MVs from HLSCs were treated with 1 U/ml RNase for 1 h at 37° C. The reaction was stopped by addition of 10 U/ml RNase inhibitor and MVs were washed by ultracentrifugation.

Cell Proliferation.

In order to investigate whether MVs derived from HLSCs exerted their anti-tumor activity on cell lines derived from a variety of tumors, MCF-7 breast adenocarcinoma cells and Kaposi's sarcoma cells were seeded at 8,000 cells/well into 96-well plates in DMEM and RPMI, respectively, with different concentrations of MVs (2; 10; 15; and 30 µg/ml and 30 µg/ml of RNase treated-MVs). DNA synthesis was detected as incorporation of 5-bromo-2'-deoxy-uridine (BrdU) into the cellular DNA after 48 hours of culture. Cells were then fixed with 0.5 M ethanol/HCl and incubated with nuclease to digest the DNA. BrdU incorporated into the DNA was detected using an anti-BrdU peroxidase-conjugated mAb and visualized with a soluble chromogenic substrate. Optical density was measured with an ELISA reader at 405 nm.

Apoptotic Assay.

MCF-7 and KS cells were seeded at 8.000 cells/well into 96-well plated in low glucose DMEM with 10% FCS and in the presence of Doxorubicin (100 ng/ml) or different concentrations of MVs (2; 10; 15; and 30 µg/ml and 30 µg/ml of RNase treated MVs). Apoptosis was evaluated using the TUNEL assay.

2.7.2 Results: MVs Derived from HLSCs Inhibit In Vitro Proliferation of MCF-7 Cells and KS Cells Incubation for 48 hours of MCF-7 breast adenocarcinoma cells and Kaposi's sarcoma cells with 2, 10, 15 and 30 µg/ml of MVs (FIGS. 16 and 17) derived from HLSC-6B cells significantly inhibits cell proliferation compared to control cells incubated with vehicle alone. These results show that the anti-tumour effects of tissue resident stem cells are not specific against tumours originated from the same tissue. Moreover, incubation of MCF-7 breast adenocarcinoma cells and Kaposi's sarcoma cells for 48 hours with 2, 10, 15 and 30 µg/ml of MVs (FIG. 18) derived from HLSC-6B cells induced apoptosis, compared to control cells incubated with vehicle alone, with effects which are similar to those of doxorubicine, a chemotherapeutic drug. This further confirms that the anti-tumour effects of tissue resident stem cells are not specific against tumours originated from the same tissue.

The invention claimed is:

1. A method of treating cancer, comprising administering to a patient in need thereof a therapeutically effective amount of a composition consisting essentially of one or more microvesicles derived from an adult human mesenchymal stem cell, wherein said treating kills cancer cells.

2. The method according to claim 1, wherein the adult stem cell is a mesenchymal stem cell selected from the group consisting of a human mesenchymal stem cell derived from bone marrow (BM-MSC) and a human mesenchymal stem cell derived from decapsulated glomeruli (Gl-MSC).

3. The method according to claim 1, wherein the cancer is selected from the group consisting of liver tumour, epithelial tumour, breast tumour, lung tumour, prostate tumour, gastric tumour, colon tumour and ovarian tumour.

4. The method according to claim 1, wherein said treating comprises administering to the patient a microvesicle dose of between 1-150 micrograms/kg body weight of the patient.

5. The method according to claim 1, wherein said treating comprises administering to the patient a microvesicle dose of between 3-120 micrograms/kg body weight of the patient.

6. The method according to claim 1, wherein the therapeutically effective amount is between 0.1 to 200 micrograms/kg body weight of the patient.

7. The method according to claim 6, wherein the one or more microvesicles are administered through a local or a systemic route.

8. The method according to claim 1 further comprising administering one or more cytotoxic and/or cytostatic agents to the patient.

9. The method according to claim 8, wherein the cytotoxic and/or cytostatic agents are selected from the group consisting of Paclitaxel, Lenalidomide, Pornalidomide, Epirubicin, 5FU, Sunitinib, La-patinib, Canertinib, cyclophosphamide, doxorubicin, Lenalidomide/Dexamethasone, Po-malidomide/Dexamethasone, Carboplatin, Rapamycin, mitoxantron, oxaliplatin, docetaxel, vinorelbin, vincristine, and a combination thereof.

10. The method according to claim 9, wherein the cytotoxic and/or cytostatic agents are doxorubicin or vincristine.

* * * * *